United States Patent … US 9,920,991 B2
Watterodt et al. … Mar. 20, 2018

(54) DEVICE FOR DRYING COATED STENTS

(71) Applicant: ABBOTT CARDIOVASCULAR SYSTEMS INC., Santa Clara, CA (US)

(72) Inventors: Sidney Watterodt, Cambridge (CA); Sang joon Park, Oakville (CA); David Rego, San Diego, CA (US); Anthony S. Andreacchi, San Jose, CA (US); Yung-Ming Chen, San Jose, CA (US); Arnoldo M. Currlin, San Jose, CA (US); Antonio Garcia, San Jose, CA (US); Jason Van Sciver, Los Gatos, CA (US); Bryan D. Glenn, Temecula, CA (US); Matthew J. Gillick, Murrieta, CA (US); John E. Papp, Temecula, CA (US)

(73) Assignees: ABBOTT CARDIOVASCULAR SYSTEMS INC., Santa Clara, CA (US); ATS AUTOMATION TOOLING SYSTEMS INC., Cambridge, Ontario (CA)

( * ) Notice: Subject to any disclaimer, the term of this patent is extended or adjusted under 35 U.S.C. 154(b) by 0 days.

(21) Appl. No.: 15/296,982

(22) Filed: Oct. 18, 2016

(65) Prior Publication Data
US 2017/0038144 A1 Feb. 9, 2017

Related U.S. Application Data

(60) Continuation of application No. 14/177,485, filed on Feb. 11, 2014, now Pat. No. 9,500,409, which is a
(Continued)

(51) Int. Cl.
F26B 25/00 (2006.01)
F26B 15/04 (2006.01)
F26B 25/06 (2006.01)
B23K 26/402 (2014.01)
F26B 15/18 (2006.01)
F26B 25/12 (2006.01)
A61F 2/91 (2013.01)
B23K 103/00 (2006.01)

(52) U.S. Cl.
CPC .......... F26B 25/003 (2013.01); B23K 26/402 (2013.01); F26B 15/04 (2013.01); F26B 15/18 (2013.01); F26B 25/06 (2013.01); F26B 25/12 (2013.01); A61F 2/91 (2013.01); B23K 2203/42 (2015.10); B23K 2203/50 (2015.10)

(58) Field of Classification Search
CPC ........ F26B 25/003; F26B 25/12; F26B 25/06; F26B 15/04; F26B 15/18; B23K 26/402; B23K 2203/42; B23K 2203/50; A61F 2/91
USPC .......................................................... 34/203
See application file for complete search history.

(56) References Cited

U.S. PATENT DOCUMENTS 5,209,181 A * 5/1993 Flood .................. B05B 13/0235
118/322
6,156,373 A * 12/2000 Zhong ....................... A61F 2/01
427/2.28
(Continued)

FOREIGN PATENT DOCUMENTS

WO WO 02091951 A2 * 11/2002 ............. A61F 2/856

Primary Examiner — Stephen M Gravini
(74) Attorney, Agent, or Firm — Squire Patton Boggs (US)

(57) ABSTRACT

Various embodiments of methods and devices for drying coated stents in an oven are described herein.

18 Claims, 14 Drawing Sheets

Related U.S. Application Data division of application No. 11/764,003, filed on Jun. 15, 2007, now Pat. No. 8,677,650.

(56) References Cited

U.S. PATENT DOCUMENTS

| | | | | |
|---|---|---|---|---|
| 6,562,136 B1* | 5/2003 | Chappa | ............... | B05B 13/0442 118/319 |
| 6,907,106 B1* | 6/2005 | McIntyre | ................. | G21G 4/08 376/157 |
| 7,211,150 B1* | 5/2007 | Kokish | .................... | A61F 2/82 118/320 |
| 8,677,650 B2* | 3/2014 | Watterodt | ............... | F26B 15/04 118/320 |
| 9,500,409 B2* | 11/2016 | Watterodt | ............... | F26B 15/04 |
| 2005/0235518 A1* | 10/2005 | Binder | ..................... | B08B 3/02 34/202 |
| 2017/0038144 A1* | 2/2017 | Watterodt | ............... | F26B 15/04 |

* cited by examiner

DEVICE FOR DRYING COATED STENTS

CROSS-REFERENCE TO RELATED APPLICATION

This application is a continuation of application Ser. No. 14/177,485, filed Feb. 11, 2014, which is a divisional of application Ser. No. 11/764,003, filed Jun. 15, 2007, now U.S. Pat. No. 8,677,650, which applications are incorporated herein by reference.

FIELD OF THE INVENTION

This invention relates to methods and devices for drying coatings on stents.

DESCRIPTION OF THE STATE OF THE ART

This invention relates to radially expandable endoprostheses, that are adapted to be implanted in a bodily lumen. An "endoprosthesis" corresponds to an artificial device that is placed inside the body. A "lumen" refers to a cavity of a tubular organ such as a blood vessel. A stent is an example of such an endoprosthesis. Stents are generally cylindrically shaped devices that function to hold open and sometimes expand a segment of a blood vessel or other anatomical lumen such as urinary tracts and bile ducts. Stents are often used in the treatment of atherosclerotic stenosis in blood vessels. "Stenosis" refers to a narrowing or constriction of a bodily passage or orifice. In such treatments, stents reinforce body vessels and prevent restenosis following angioplasty in the vascular system. "Restenosis" refers to the reoccurrence of stenosis in a blood vessel or heart valve after it has been treated (as by balloon angioplasty, stenting, or valvuloplasty) with apparent success.

Stents are typically composed of scaffolding that includes a pattern or network of interconnecting structural elements or struts, formed from wires, tubes, or sheets of material rolled into a cylindrical shape. This scaffolding gets its name because it physically holds open and, if desired, expands the wall of the passageway. Typically, stents are capable of being compressed or crimped onto a catheter so that they can be delivered to and deployed at a treatment site. Delivery includes inserting the stent through small lumens using a catheter and transporting it to the treatment site. Deployment includes expanding the stent to a larger diameter once it is at the desired location. Mechanical intervention with stents has reduced the rate of restenosis as compared to balloon angioplasty. Yet, restenosis remains a significant problem. When restenosis does occur in the stented segment, its treatment can be challenging, as clinical options are more limited than for those lesions that were treated solely with a balloon.

Stents are used not only for mechanical intervention but also as vehicles for providing biological therapy. Biological therapy uses medicated stents to locally administer a therapeutic substance. Effective concentrations at the treated site require systemic drug administration which often produces adverse or even toxic side effects. Local delivery is a preferred treatment method because it administers smaller total medication levels than systemic methods, but concentrates the drug at a specific site. Local delivery thus produces fewer side effects and achieves better results.

A medicated stent may be fabricated by coating the surface of a stent with an active agent or an active agent and a polymeric carrier. Those of ordinary skill in the art fabricate coatings by applying a polymer, or a blend of polymers, to the stent using well-known techniques. Such a coating composition may include a polymer solution and an active agent dispersed in the solution. The composition may be applied to the stent by immersing the stent in the composition, by printing, or by spraying the composition onto the stent. All or most of the solvent is removed by drying methods that cause the solvent to evaporate, leaving on the stent surfaces a polymer coating impregnated with the drug or active agent. The processing parameters of the each step of the coating process, such as drying, influence the microstructure of the coating which can have a great impact to the coating quality and drug release profile. In addition, throughput and efficiency of the coating process is also of concern.

SUMMARY OF THE INVENTION

Briefly and in general terms, the present invention is directed to a device for drying coated stents.

In aspects of the invention, a device comprises an oven enclosure including a rotatable dial configured ti carry stent supports within the oven enclosure so that the stents on the stent supports can be conveyed by rotation of the dial within the oven enclosure to dry a coating on the stents, and a transfer mechanism including an actuator and a first gripper, the actuator configured to move the first gripper into and out of the oven enclosure, the first gripper configured to remove a stent support from the dial.

In aspects of the invention, a device comprises an oven enclosure, and a conveyer belt disposed within the oven enclosure, wherein the conveyer belt is configured to support a plurality of coated stents so that the stents can be conveyed within the oven enclosure to dry a coating on the stents, the stents conveyed through movement of the belt through the oven enclosure.

DETAILED DESCRIPTION OF THE INVENTION

Embodiments of the present invention relate to coating implantable medical devices such as stents. In particular, the embodiments of the present invention relate to aspects of methods and devices for drying the coating material applied to stents. Embodiments of the present invention may be used in coating devices including, but not limited to, self-expandable stents, balloon-expandable stents, stent-grafts, vascular grafts, cerebrospinal fluid shunts, pacemaker leads, closure devices for patent foramen ovale, and synthetic heart valves.

In particular, a stent can have virtually any structural pattern that is compatible with a bodily lumen in which it is implanted. Typically, a stent is composed of a pattern or network of circumferential and longitudinally extending interconnecting structural elements or struts. In general, the struts are arranged in patterns, which are designed to contact the lumen walls of a vessel and to maintain vascular patency. A myriad of strut patterns are known in the art for achieving particular design goals. A few of the more important design characteristics of stents are radial or hoop strength, expansion ratio or coverage area, and longitudinal flexibility. Embodiments of the present invention are applicable to virtually any stent design and are, therefore, not limited to any particular stent design or pattern. One embodiment of a stent pattern may include cylindrical rings composed of struts. The cylindrical rings may be connected by connecting struts.

In some embodiments, a stent may be formed from a tube by laser cutting the pattern of struts in the tube. The stent may also be formed by laser cutting a metallic or polymeric sheet, rolling the pattern into the shape of the cylindrical stent, and providing a longitudinal weld to form the stent. Other methods of forming stents are well known and include chemically etching a metallic or polymeric sheet and rolling and then welding it to form the stent.

In other embodiments, a metallic or polymeric filament or wire may also be coiled to form the stent. Filaments of polymer may be extruded or melt spun. These filaments can then be cut, formed into ring elements, welded closed, corrugated to form crowns, and then the crowns welded together by heat or solvent to form the stent.

Figure 1:
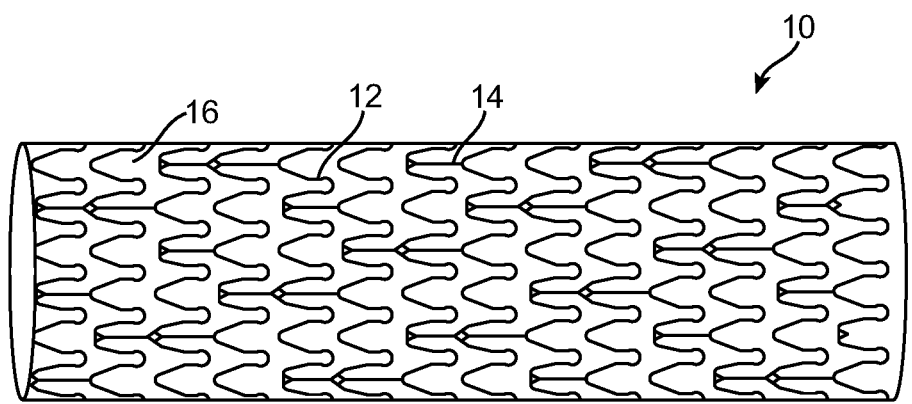
FIG. 1 depicts a cylindrically-shaped stent.

FIG. 1 illustrates a conventional stent 10 formed from a plurality of struts 12. The plurality of struts 12 are radially expandable and interconnected by connecting elements 14 that are disposed between adjacent struts 12, leaving lateral openings or gaps 16 between adjacent struts 12. Struts 12 and connecting elements 14 define a tubular stent body having an outer, tissue-contacting surface and an inner surface.

The cross-section of the struts in stent 10 may be rectangular- or circular-shaped. The cross-section of struts is not limited to these, and therefore, other cross-sectional shapes are applicable with embodiments of the present invention. Furthermore, the pattern should not be limited to what has been illustrated as other stent patterns are easily applicable with embodiments of the present invention.

As indicated above, a medicated coating on a stent may be fabricated by spraying a coating composition including polymer and drug on the stent. Spray coating a stent typically involves mounting or disposing a stent on a support, followed by spraying a coating material from a nozzle onto the mounted stent.

A spray apparatus, such as EFD 780S spray device with VALVEMATE 7040 control system (manufactured by EFD Inc., East Providence, R.I., can be used to apply a composition to a stent. A EFD 780S spray device is an air-assisted external mixing atomizer. The composition is atomized into small droplets by air and uniformly applied to the stent surfaces. Other types of coating applicators, including air-assisted internal mixing atomizers (such as IVEK SonicAir nozzle), ultrasonic applicators (such as Accu-Mist nozzle or MicroMist nozzle from SOnoTEk Co. in Milton, N.Y.), or drop dispensing device can also be used for the application of the composition.

To facilitate uniform and complete coverage of the stent during the application of the composition, the stent can be rotated about the stent's central longitudinal axis. Rotation of the stent can be from about 0.1 rpm to about 300 rpm, more narrowly from about 30 rpm to about 200 rpm. By way of example, the stent can rotate at about 150 rpm. The stent can also be moved in a linear direction along the same axis. The stent can be moved at about 1 mm/second to about 30 mm/second, for example about 6 mm/second, or for a minimum of at least two passes (i.e., back and forth past the spray nozzle). In other applications, the spray nozzle can be devised to translate over the stent. The stent is rotated at a desired speed underneath the nozzle.

A nozzle can deposit coating material onto a stent in the form of fine droplets. An atomization pressure of a sprayer can be maintained at a range of about 5 psi to about 30 psi. The droplet size depends on factors such as viscosity of the solution, surface tension of the solvent, solution feed rate, and atomization pressure. The flow rate of the composition from the spray nozzle can be from about 0.01 mg/second to about 1.0 mg/second, for example about 0.1 mg/second. Only a small percentage of the composition that is delivered from the spray nozzle is ultimately deposited on the stent depending on the transfer efficiency of the spray setup. By way of example, when a composition is sprayed to deliver about 1 mg of solids, only about 100 micrograms or about 10% of the solids sprayed will likely be deposited on the stent. The solid percent in the composition typically can range from 0.1 wt % to 15 wt %, for example about 5 wt %.

To reduce or eliminate coating defects in coated stents, excessive solvent is removed from applied coating material through an in-process drying cycle. Excessive application of the polymer or excessive solvent left in the coating can cause coating defects such as pool web (excessive material accumulated between stent struts) due to the lack of good wettability of the coating droplets over a stent with a tight geometry.

The coating process can involve multiple repetitions of spraying forming a plurality of layers. A repetition can involve a single pass or multiple passes of moving a spray nozzle (or moving the stent), a pass being from one end (e.g., proximal end) to the other end (e.g., distal end) of a stent. Each repetition can be, for example, about 0.5 second to about 20 seconds, for example about 10 seconds in duration. The amount of dry coating applied by each repetition can be about 1 microgram/cm$^2$ (of stent surface) to about 75 micrograms/cm$^2$, for example less than about 20 micrograms/cm$^2$.

As indicated above, the coating composition can include a polymer dissolved in a solvent. Each repetition can be followed by in-process drying involving removal of a significant amount of the solvent(s). In an embodiment, there may be less than 5%, 3%, or more narrowly, less than 1% of solvent remaining in the coating after drying between repetitions. Between repetitions, some or all of the solvent can be removed from the coating material on the stent by subjecting the stent to an in-process drying process. Any suitable number of repetitions of applying the composition followed by removing the solvent(s) can be performed to form a coating of a desired thickness or weight.

A stent coated with coating material can be dried by allowing the solvent to evaporate at room or ambient temperature. Depending on the volatility of the particular solvent employed, the solvent can evaporate essentially upon contact with the stent. Alternatively, the solvent can be removed by subjecting the coated stent to various drying processes. Between repetitions, for instance, room temperature or a warm gas can be blown onto the coated stent to remove solvent. Solvent can also be removed by baking the stent in an oven at a mild temperature (e.g., 60° C.) for a suitable duration of time (e.g., 2-4 hours) or by the application of warm air. There can be some residual solvent left in the coating after the in-process drying depending on the solvent used and in-process drying time. The higher the boiling point of the solvent, the harder it is to remove solvent in the in-process drying process. The coated stent is typically dried in an oven as the final drying step when the multiple deposition stages are completed to remove residual solvent. The residual solvent can have harmful biological effects and plasticizing effects which can alter the release rate and coating properties. The energy source of the oven can range from a convection oven to an infrared oven or UV.

Various embodiments of the present invention are directed to a device and methods for drying and/or curing the coating material applied to a stent. In particular, these embodiments of the invention are intended to improve the oven drying or curing process repeatability for drug-eluting stent manufacturing. In a conventional manufacturing process, stents are spray coated with a drug-polymer solution and manually placed into clean room ovens for the final drying or curing of the coating. The bake time is typically 30 to 60 minutes. The spray coating process produces one stent at a time, and the stents are individually loaded into the ovens by operators where stents are queued into batches for baking.

There are several drawbacks to the conventional process. One drawback is that the operator must repeatedly open the oven door to add and remove stents from the oven which can prevent the temperature profile in the oven from reaching a steady state. This can cause temperature fluctuations that can adversely affect other stents in the batch. The door opening may not be controlled, and may occur at varying time intervals. Variations in door opening times can result in inconsistencies in temperature exposure of drying stents.

Another drawback of a conventional process is that the operator typically manually keeps track of the drying time for each stent in the oven and must take care not to mix up the order of stent addition or removal from the oven. Thus, control of drying time depends upon the operator which can lead to small and, potentially, large inconsistencies in drying time.

Still a further drawback of the conventional process is that stents may be placed in different locations within the oven, leading to differences in baking temperature and/or differences in convection air exposure. Thus, the temperature history of a stent depends on its location in the oven. An additional drawback of the conventional process is that each time the oven door is opened, the stents in the oven are exposed to possible particulate contamination.

Various embodiments of the present invention described below reduce or eliminate the drawbacks of a conventional drying process. The variation in temperature due to door opening is reduced or eliminated. In addition, embodiments eliminate the need for an operator to track stents and baking times. Furthermore, each stent is exposed to the same temperature profile in the oven.

Figure 2:
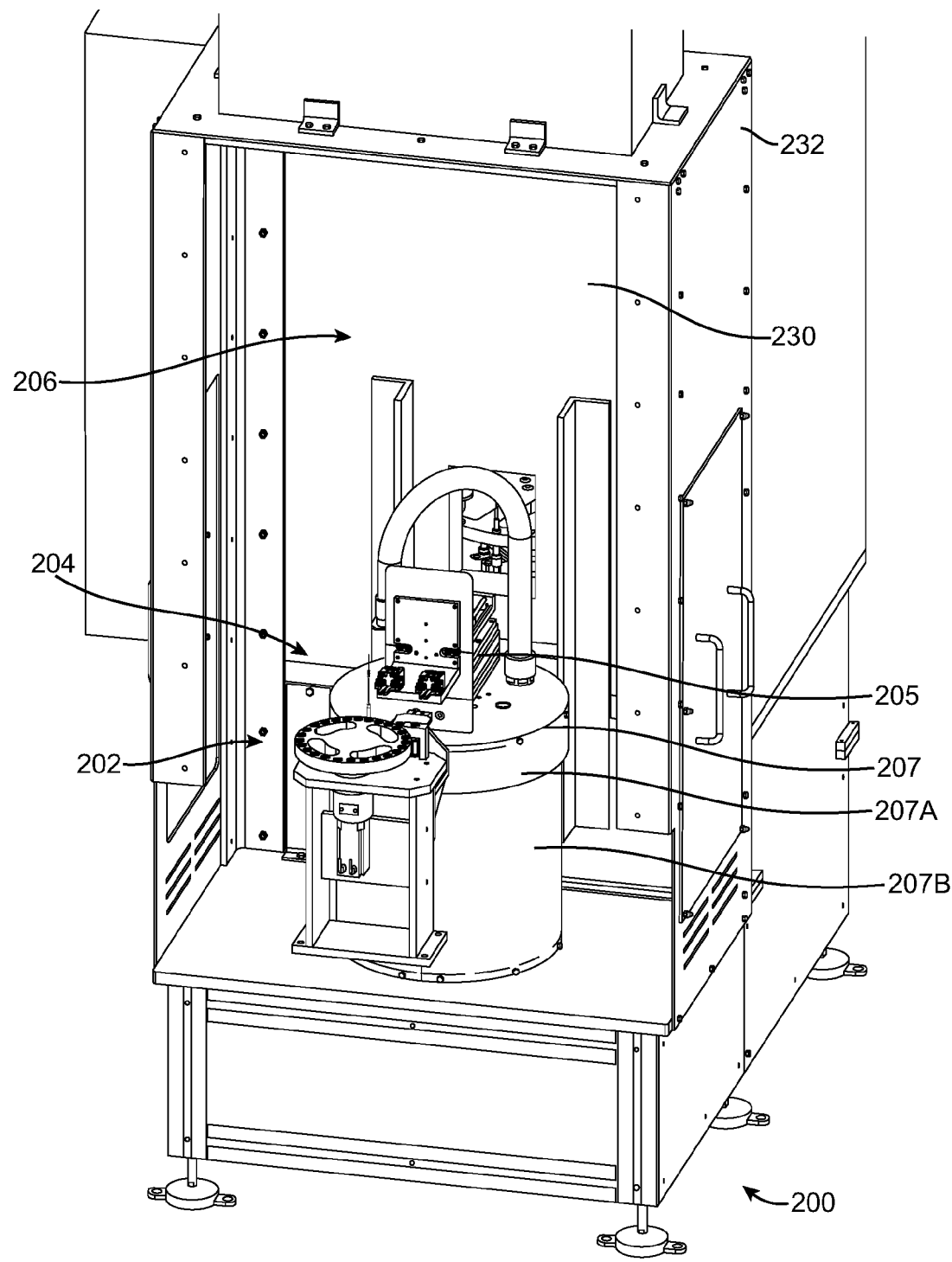
FIG. 2 depicts an exemplary drying device.

Embodiments of the present invention may be illustrated by the exemplary drying device 200 depicted in FIG. 2. Device 200 includes a buffer mechanism 202, a transfer mechanism 204, and a drying mechanism or oven 206. Oven 206 is defined by an enclosure composed of a front wall 230, side walls 232, and a back wall (not shown).

Device 200 can be used in conjunction with any spray coating process. Coated stents can be manually positioned into buffer mechanism 202 for drying. Alternatively, device 200 can be a module of an automated process which includes two or more modules designed to coat stents. For example, in an automated system, a robotic arm with grippers can place a stent in buffer mechanism 202 and a robotic arm with grippers can remove a dried stent from buffer mechanism 202.

Figure 3:
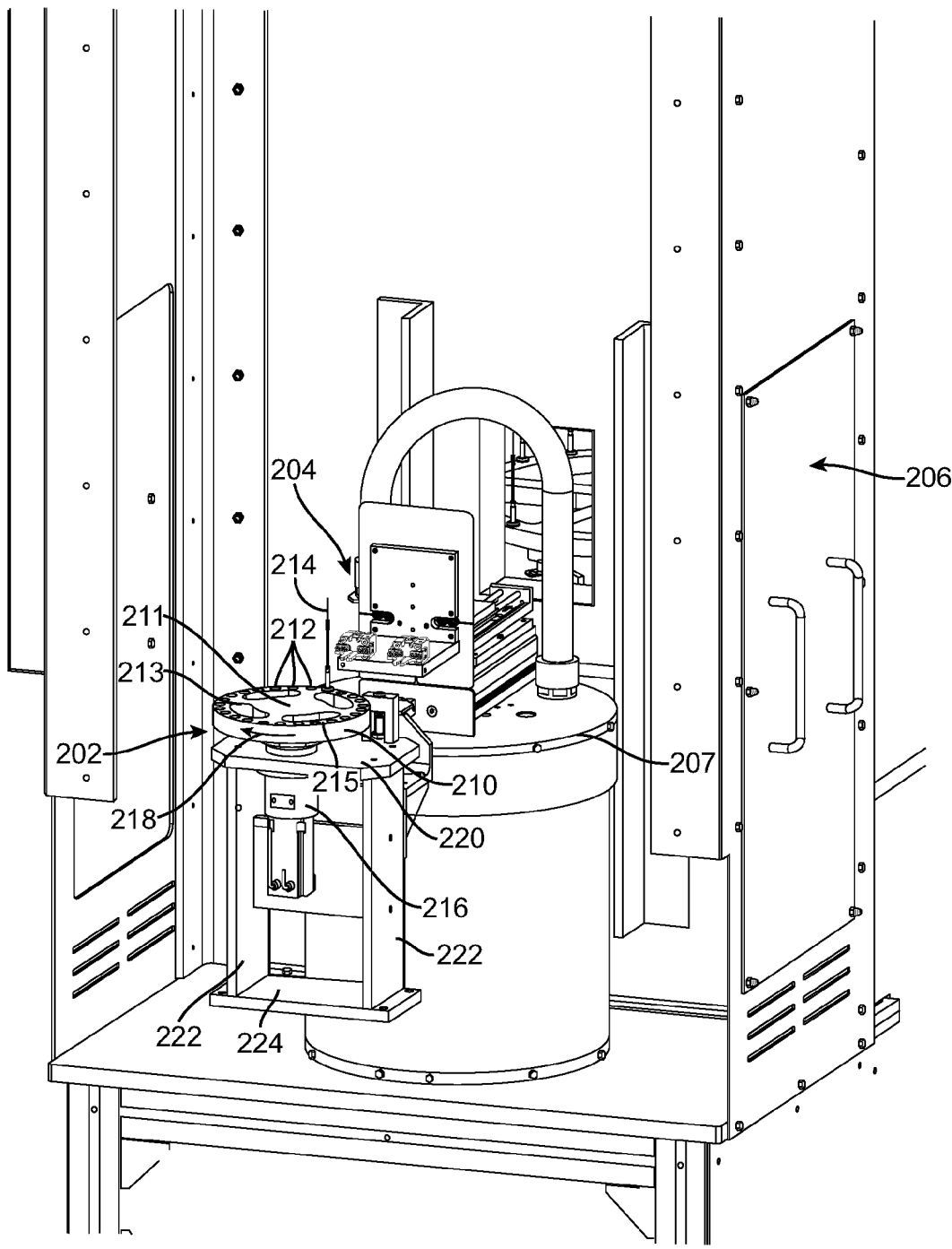
FIG. 3 depicts a close-up view of a drying device.

FIG. 3 depicts a close-up view of device 200. Buffer mechanism 202 includes a buffer dial 210. Stents for drying are loaded onto buffer dial 210 to await transfer to drying mechanism 206 for drying and are transferred via transfer mechanism 204. In a case in which the coating process is faster than the drying process, buffer dial 210 acts as a buffer between a coating process prior to drying and the drying process. Stents are stored on buffer dial 210, since stents are generally supplied to the drying process faster than the stents can be dried. Stents that have been dried in drying mechanism 206 are transferred to buffer mechanism 202, where they await to be transferred out from device 200.

Buffer dial 210 includes a center 211 with spokes 213 radiating outward to a peripheral region 215. Peripheral region 215 includes a plurality of holes or nests 212 for holding stent supports, such as stent support 214, on which stents are mounted. Buffer dial 210 is coupled to a rotary spindle 216 that rotates buffer dial 210 as shown by arrow 218. Rotary spindle 216 can be configured to rotate buffer dial 210 in an indexing or discrete fashion or continuously. The storage capacity of stents in buffer mechanism 202 can be increased by replacing buffer dial 210 with one with a greater circumference and having a larger number of holes for storing stents. Buffer dial 210 can be releasable coupled to rotary spindle 216, e.g., with screws, etc., to enable switching out of one buffer dial for another. Buffer dial 210 is mounted on a housing including a mounting plate 220, two side plates 222, and a bottom plate 224.

Figure 4:
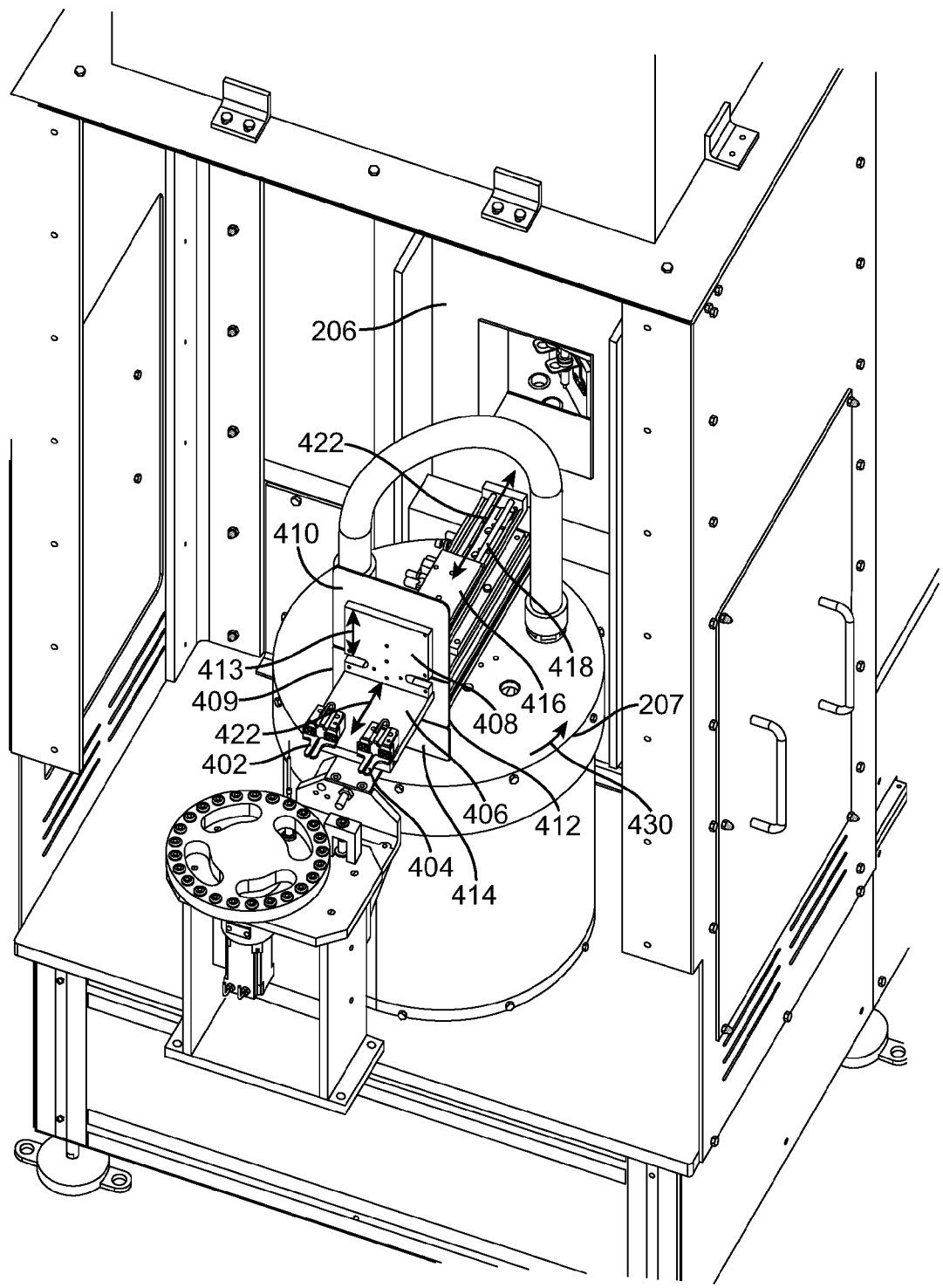
FIG. 4 depicts a close-up view of a transfer mechanism of a drying device.

As noted above, stents are transferred from buffer mechanism 202 to drying mechanism 206 via transfer mechanism 204. As shown in FIG. 2, transfer mechanism 204 includes a transfer unit 205 mounted on a rotatable mounting plate 207. Mounting plate 207 is supported by cylindrical shields 207A and 207B. FIG. 4 depicts a close-up view of transfer mechanism 204. Transfer mechanism 204 includes grippers 402 and 404. Gripper 402 grips a stent support disposed in buffer dial 210, removes the gripped stent support from buffer dial 210, and carries the gripped stent support to drying mechanism 206. Gripper 404 carries a gripped stent from drying mechanism 206 and places it in buffer dial 210 to await removal from device 200 by a gripping device controlled by a robotic arm or that is manually directed. Gripper devices such as those depicted in FIG. 4 are well known to those of skill in the art of automated processing of parts.

Grippers 402 and 404 are mounted on gripper plate 406. Gripper plate 406 is mounted perpendicular relative to vertical wall 408 which is mounted on a shield 409. Shield 409 is in four parts: a baffle top 410, a baffle bottom 412, and two lower shields 414. Gripper plate 406 is coupled to an actuator which can move gripper plate 406 up and down, as shown by an arrow 413, along with grippers 402 and 404 to allow the grippers to remove and place stent supports on and from buffer dial 210 and oven dial 702 (described below). The distal end of gripper plate 406 is coupled to a slider plate 416 which is mounted on an actuator 418 that moves slider plate 416 and gripper plate 406 as shown by arrows 420 and 422, respectively.

Figure 5:
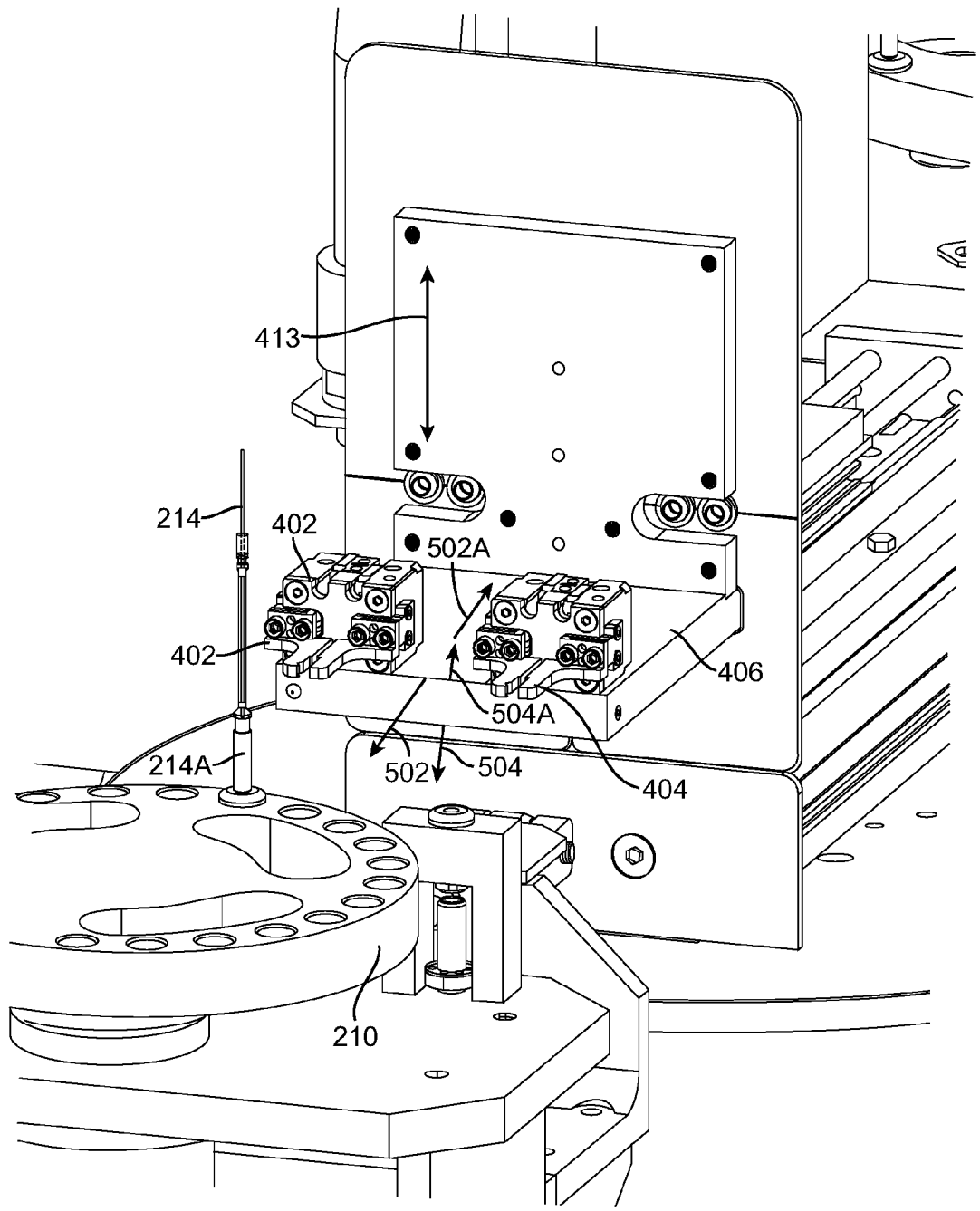
FIG. 5 depicts a close-up view of the transfer mechanism of FIG. 4 in the proximity of stent grippers.

FIG. 5 depicts a close-up view of FIG. 4 focused in the proximity of grippers 402 and 404. To grip and remove stent support 214, gripper plate 406 moves toward buffer dial 210 and downward, as shown by arrows 502 and 504, respectively, so that gripper 402 can grip and remove a stent support 214 which is carrying a stent ready for drying. Gripper plate 406 moves to position gripper 402 so that it can grip stent support 214 at its distal end 214A.

Gripper plate 406 can also be moved so that gripper 404 can deposit a stent support (not shown) with a dried stent in one of holes 212. After gripping stent support 214 with gripper 404, gripper plate 406 actuates upwards, as shown by an arrow 504A, to remove stent support 214 from buffer dial 210. Gripper plate 406 is then actuated in the direction of an arrow 502A.

Figure 6:
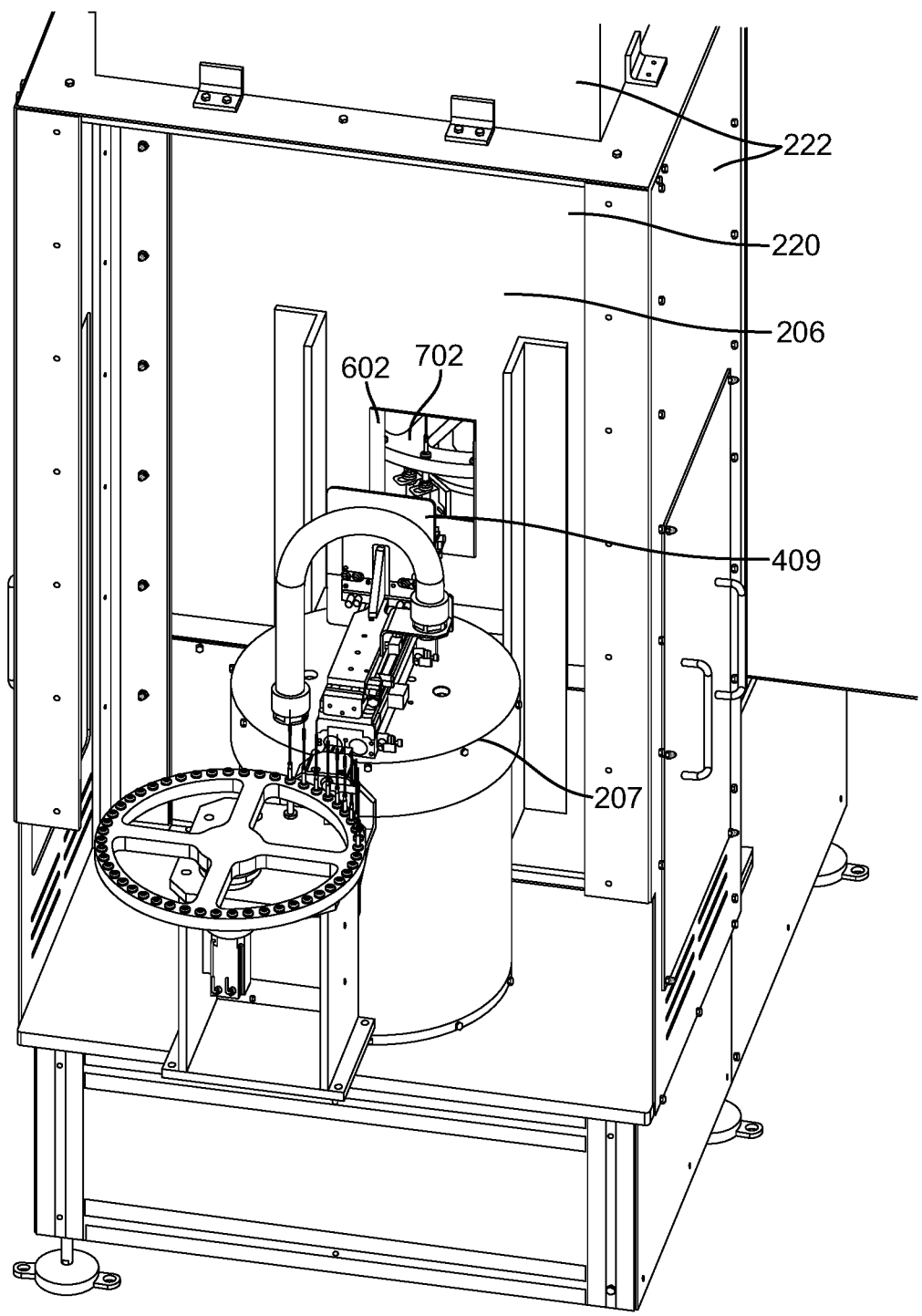
FIG. 6 depicts a view of the transfer mechanism of FIG. 4 with 9 mounting plate rotated 180° from the position shown in FIGS. 2-5.

As shown by arrow 430 in FIG. 4, rotatable mounting plate 207 can rotate to position grippers 402 and 404 so that gripper 402 can place a stent support in oven 206 and gripper 404 can remove a dried stent from oven 206. Gripper 402 can also remove stents from the oven. For example, if a processing sequence is aborted, gripper 402 can be used to remove all stents from oven 206. FIG. 6 depicts a view of transfer mechanism 204 with mounting plate 207 rotated 180° from the position shown in FIGS. 2-5 showing the back face of shield 409. In this position, grippers 402 and 404 (not shown) are facing oven 206. Oven 206 includes a window 602 through which the interior of oven 206 is accessible by grippers 402 and 404.

Figure 7:
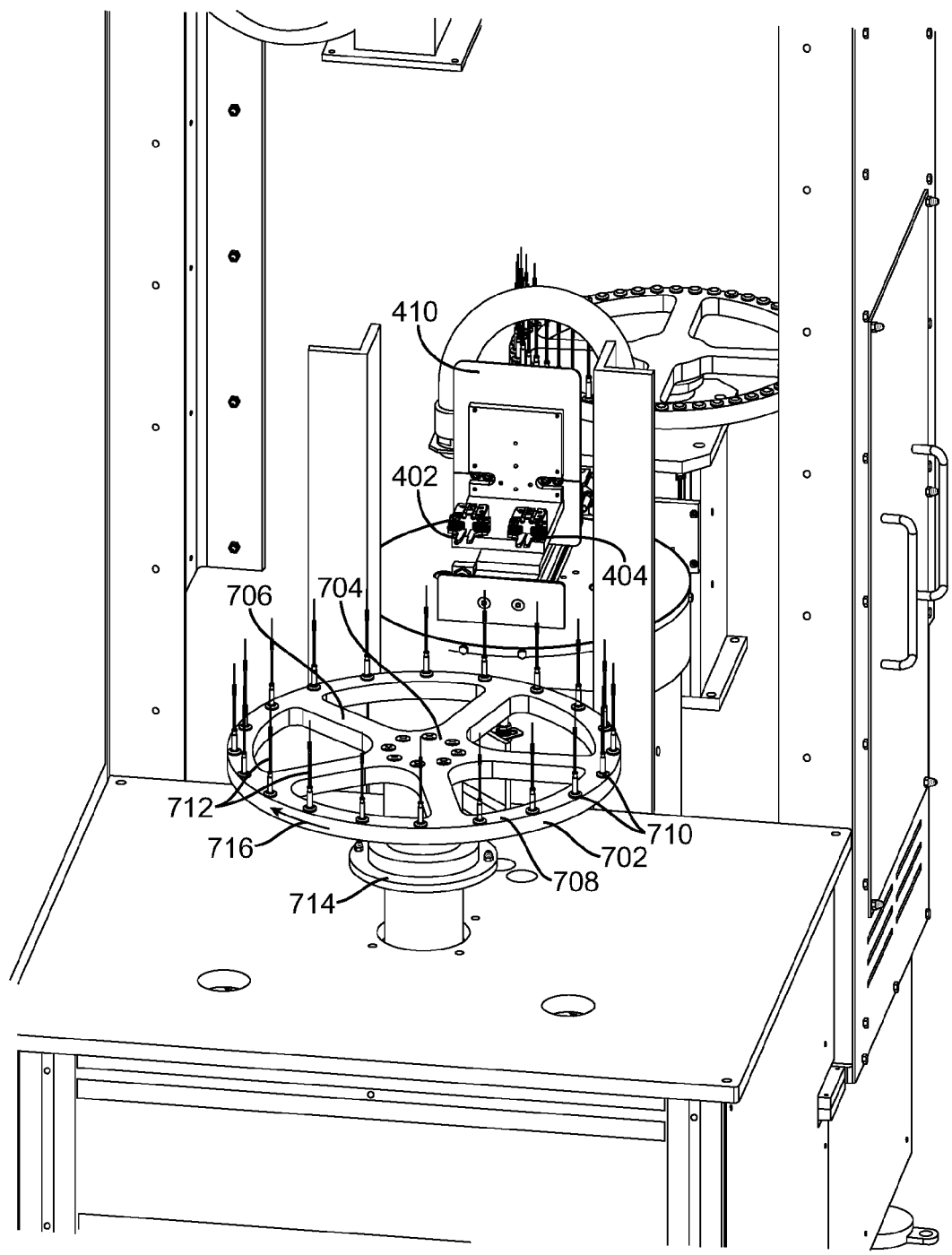
FIG. 7 depicts of view looking through the back of device 200 shown in FIG. 6 with the back and side walls removed.

As indicated in FIG. 2, oven 206 is defined by an enclosure composed of a front wall 230, side walls 232, and a back wall (not shown). FIG. 7 depicts of view looking through the back of device 200 shown in FIG. 6 with the back and side walls removed. Oven 206 can be a modified commercially available oven suitable for drying a coated medical device such as a stent. For example, a commercially available or specially modified forced-air convection oven can be used. An exemplary oven is a Despatch LAC1-10 forced-air convection oven, from Despatch Industries, Lakeville, Minn. The modifications are described below.

Device 200 includes a door (not shown) for covering window 602. The door can cover or seal window 602 during the periods between placement and removal of stents from oven 206. Device 200 includes a "guillotine" door that closes from bottom to top of window 602 or opens from top to bottom. The opening and closing of the door in this manner reduces or prevents generation of particles due to the movement of the door. Such particles can contaminate the coated stents. Alternatively, the door can open from bottom to top or the door can swing open and close from the sides, top, or bottom of the opening. The door acts as a thermal barrier to reduce or prevent thermal energy from escaping from the oven. Heat transferred through window 602 can adversely affect the coating quality of stents stored in device 200 or coating quality of stents or coating operation adjacent to device 200. Reducing or preventing heat transfer through window 602 also provides for a more uniform temperature within oven 206 and less variability of temperature within oven 206.

Referring to FIG. 7, device 200 includes an oven dial 702 for holding stents during drying within oven 206. Oven dial 702 includes a center 704 with spokes 706 radiating outward to a peripheral region 708. Peripheral region 708 includes a plurality of holes or nests 710 for holding stent supports 712 on which stents are mounted. Oven dial 702 is mounted on a rotary spindle 714 which rotates oven dial 702 as shown by an arrow 716. Rotary spindle 714 can rotate oven dial 702 in an indexing fashion, i.e., a discrete step-wise movement.

Figure 8:
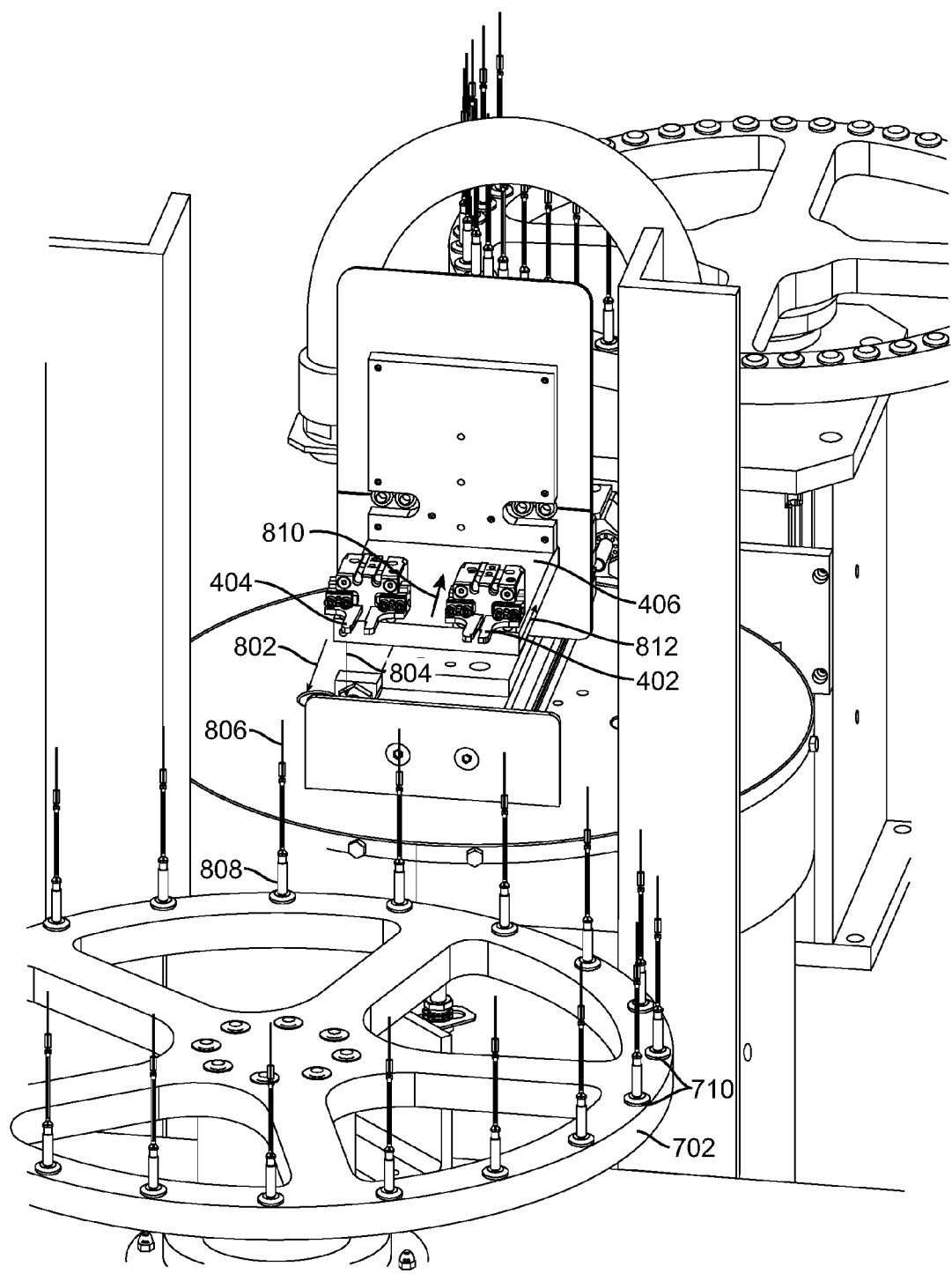
FIG. 8 depicts a close-up view of the oven dial in the proximity of stent grippers.

Dual grippers 402 and 404 allow removal of a dried stent from oven dial 702 and placement of a stent in oven dial 702. FIG. 8 depicts a close-up view of oven dial 702 in the proximity of grippers 402 and 404. Gripper plate 406 can move toward oven dial 702 and downward, as shown by arrows 802 and 804, so that gripper 402 can grip and remove a stent support carrying a dried stent. Gripper plate 406 is moved to position gripper 402 so that it can grip a stent support 806 at its distal end 808. Gripper plate 406 is also moved so that gripper 404 can deposit a stent support with an undried stent in one of holes 710. After gripping a stent support with gripper 402, gripper plate 406 is actuated upwards as shown by arrow 810, to remove the stent support from oven dial 702. Gripper plate 406 is then actuated in the direction of arrow 812.

Transfer mechanism 204 can be operated in such a way that one of gripper 404 or 402 is carrying a stent either to or from oven 206, respectively. When operating in this fashion, each time gripper 404 deposits a stent support in oven dial 702, gripper 402 removes a stent support from oven dial 702, if a stent support is available to remove. In addition, each time gripper 402 deposits a stent support in buffer dial 210, gripper 404 removes a stent support from buffer dial 210, if a stent support is available to remove.

The residence time of a stent support on oven dial 702 depends on the size or circumference of oven dial 702 and the indexing rate of oven dial 702. The larger the circumference of oven dial 702, the longer is the residence time of a stent on a stent support on oven dial 702. Oven dial 702 can be releasably coupled to rotary spindle 714, e.g., with screws, etc., to enable switching out of one oven dial for another. In addition, the slower the indexing rate of oven dial 702, the longer is the residence time. The residence time can be programmable and adjustable.

The polymer and drug in the stent coating can be very sensitive to temperature. Both the polymer and the drug can degrade in an undesirable manner. Additionally, it is important for drying conditions to be consistent from stent to stent since such variability in temperature can affect the properties of the coating.

Several features of oven 206 described herein reduce variations in temperature that can degrade the coating and that provide for consistent drying of stents. The guillotine door reduces or eliminates temperature variations in oven 206 between the stent placement and removal steps. In addition, the motion of the rotary oven dial 702 results in the same temperature exposure of each stent. This results in consistency in temperature exposure from stent to stent. Additionally, oven 206 includes numerous temperature probes (not shown) that continuously or discretely monitor the temperature. Temperature controllers (not shown) control the temperature based on the monitored temperature and desired temperature. A desired temperature in the oven can be at least 40° C., 50° C., 60° C., or at least 80° C.

Furthermore, the temperature can be recorded and stored at any time or during regular or irregular intervals. The temperature at such intervals can be associated with individual stents in oven 206 so that there is a temperature history for individual stents. For example, the temperature can be recorded for a stent when it is placed in an oven and when it is removed from an oven.

Figure 9:
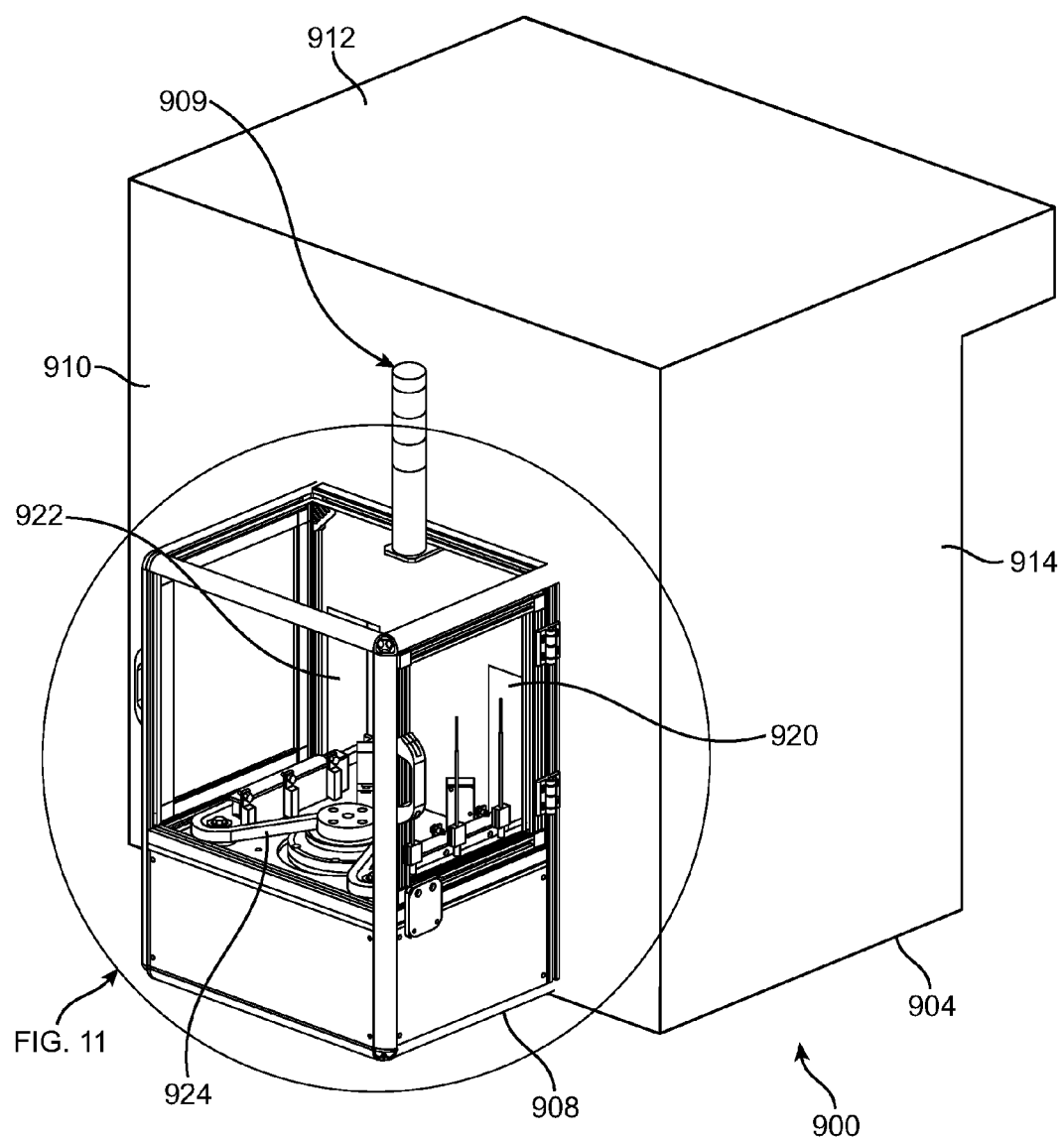
FIG. 9 depicts another exemplary drying device.
Figure 10:
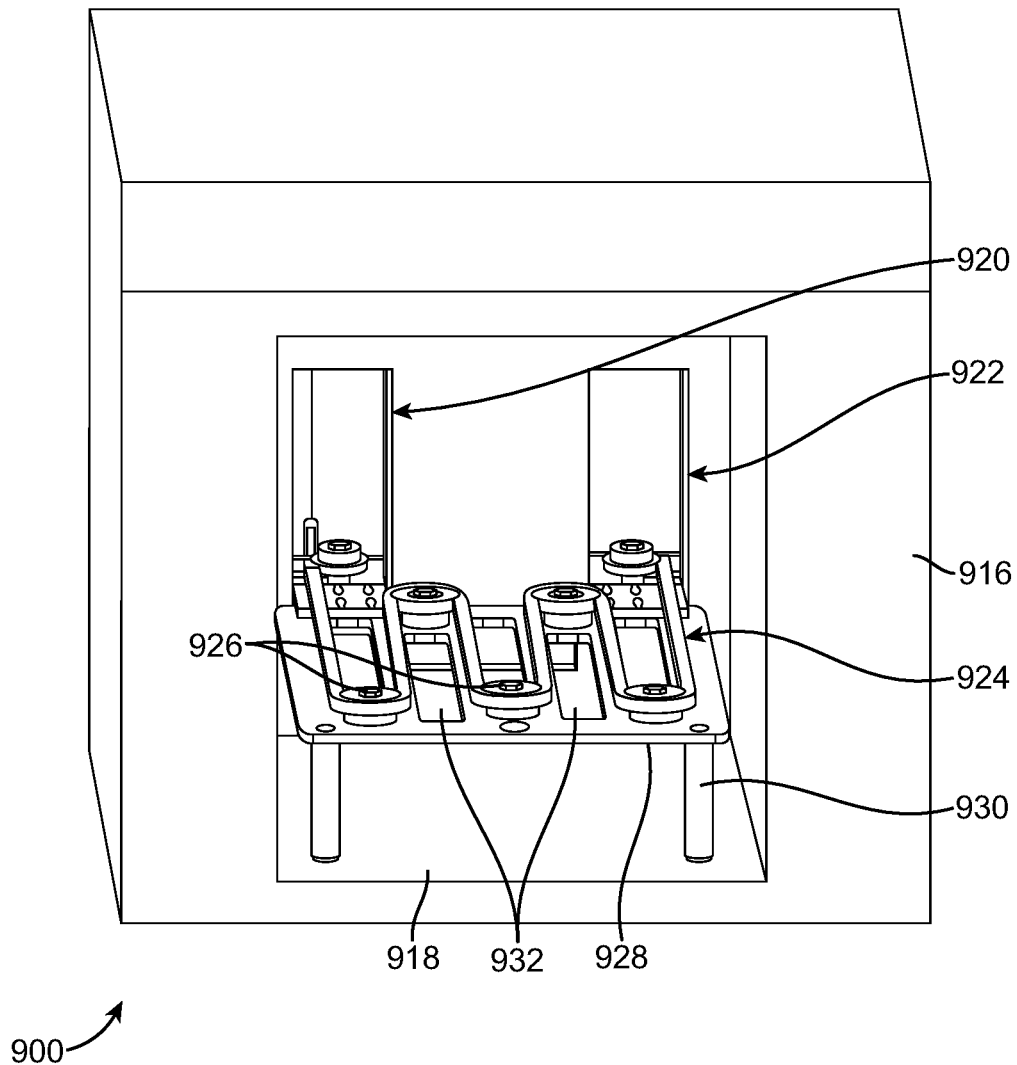
FIG. 10 depicts a rear view of the exemplary drying device shown in FIG. 9 showing the interior of an oven enclosure.
Figure 11:
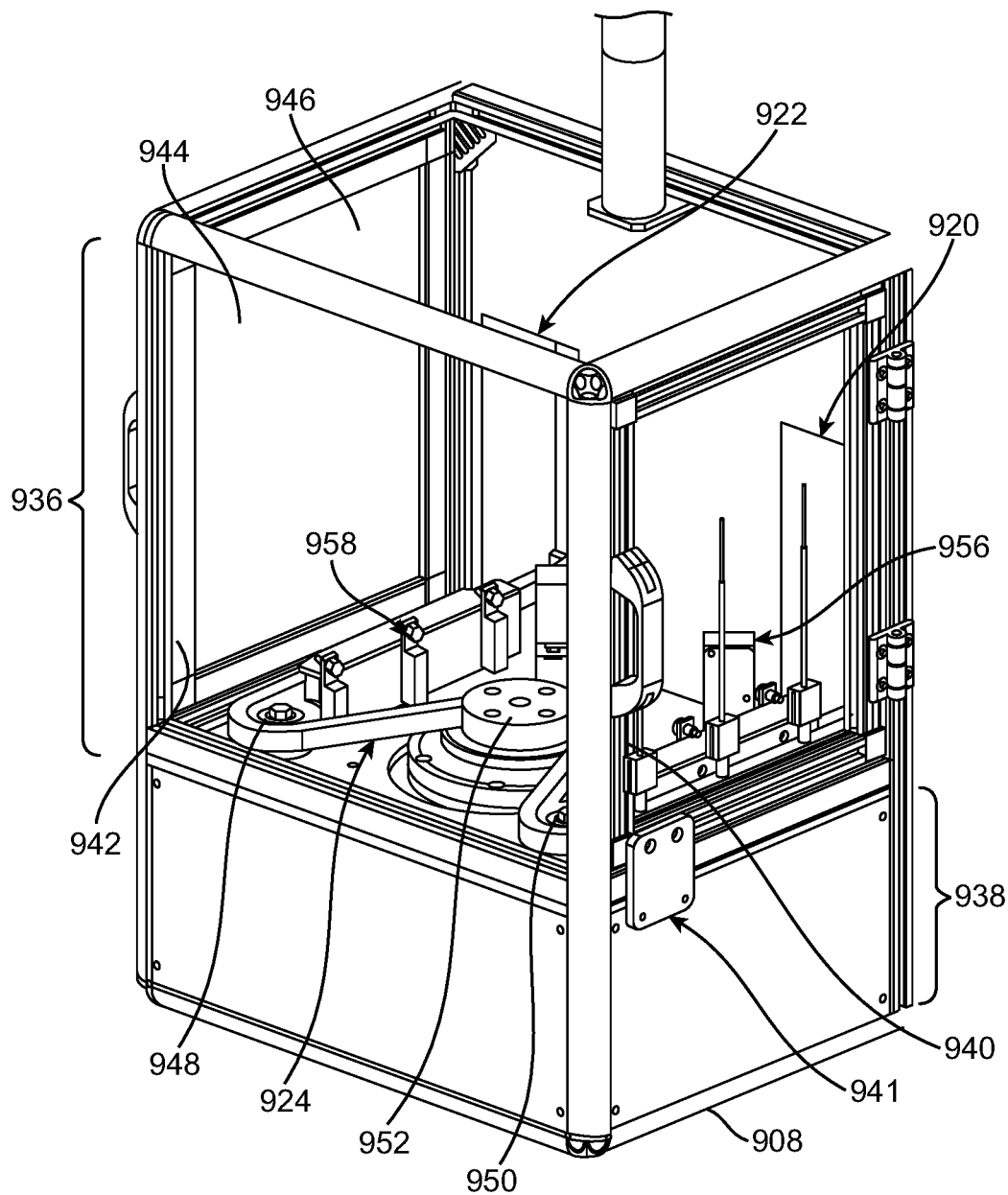
FIG. 11 depicts a close-up view of a loading enclosure of the stent drying device shown in FIG. 9.
Figure 12:
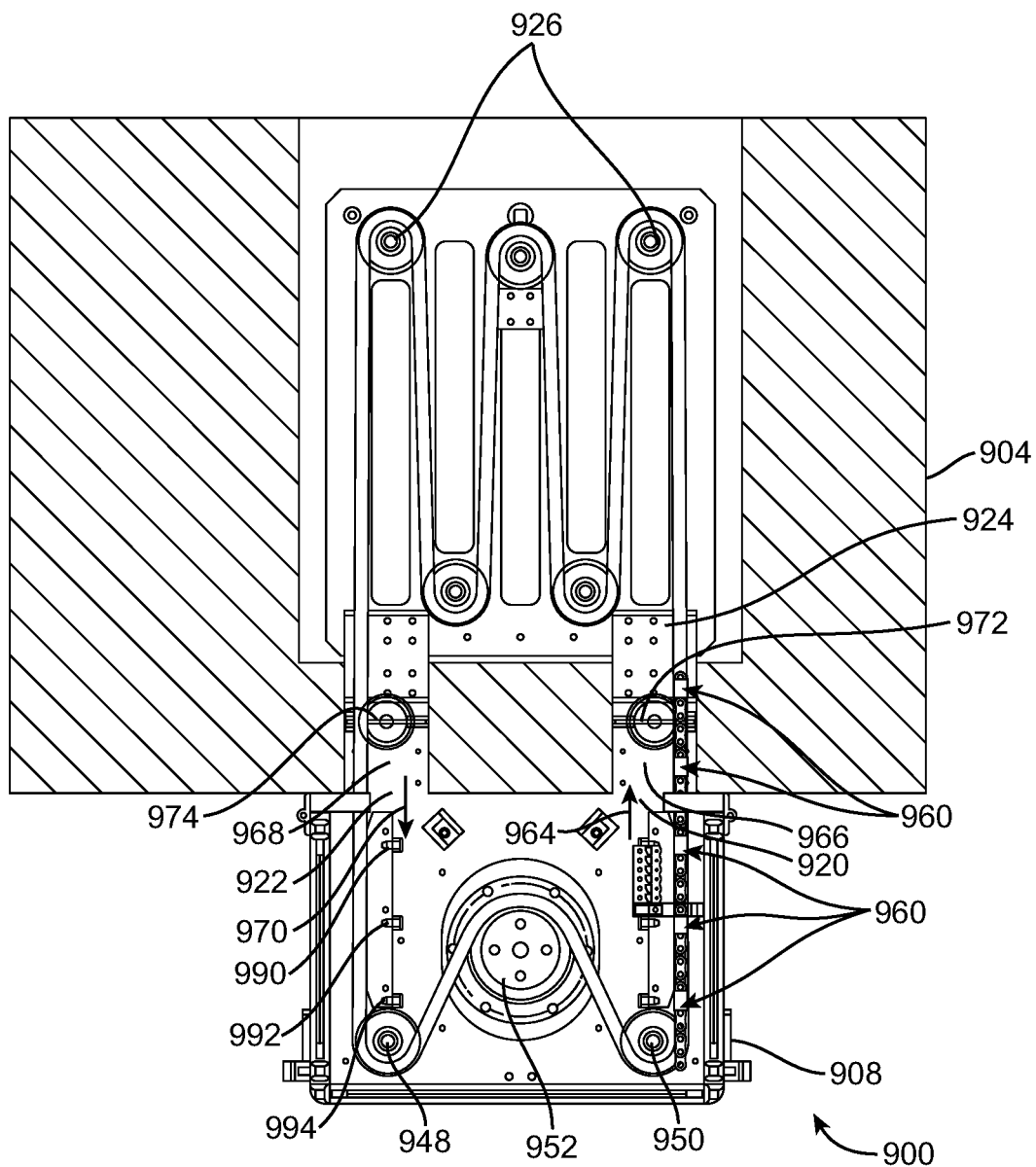
FIG. 12 depicts a top view of the drying device shown in FIG. 9.

FIGS. 9-12 depict another exemplary embodiment of a drying device 900. As shown in FIG. 9, device 900 includes two sections or portions, an oven 904 and a loading enclosure 908. FIG. 10 depicts a rear view of device 900 showing the interior of oven 904. FIG. 11 depicts a close-up view of loading enclosure 908. FIG. 12 depicts a top-sectional view of device 900 shown in FIG. 9.

Oven 904 can be a modified commercially available oven suitable for drying a coated medical device. For example, a model CR1 clean room oven, manufactured by Sheldon Manufacturing Inc. of Cornelius, Oreg., can be modified in the manner described below. Oven 904 includes an oven enclosure with a front wall 910, top wall 912, a bottom wall (not shown), side walls 914, and a rear wall 916. Rear wall 916 has an opening 918 and a door that seals the opening. The door has been removed to show the interior of the oven enclosure. Oven 904 also includes two rectangular front openings 920 and 922 in front wall 910 which are visible in FIG. 9 and through the interior of the oven enclosure in FIG. 10.

As shown in FIG. 10, device 900 includes a conveyor belt or chain 924 for transporting stents into oven 904 from loading enclosure 908, through oven 904, and out of oven 904 back into loading enclosure 908. Conveyor belt 924 follows a zig-zag pattern in the oven interior. Other paths can be used, for example, round oval, rectangular, combinations thereof, etc.

Conveyor belt or chain 924 can be made up of links or perforations so that it can be directed or driven through the oven enclosure using gears 926 with teeth which are supported on a plate 928. Plate 928 is supported on the floor of oven 904 by elongate members 930. Plate 928 includes openings 932 that allow for circulation of air within the oven enclosure. Conveyer belt 924 can also be "featureless", possessing no perforations. Featureless gears can be driven and guided by gears without teeth. Exemplary belts can be obtained from Belt Technologies, Inc. in Agawam, Mass.

Referring to FIG. 11, stents can be loaded onto device 900 into loading enclosure 908. Loading enclosure 908 has a top section 936 supported by a bottom section 938. Loading enclosure 908 has an access door 940 that allows access to the interior of loading enclosure 908 to load stents on conveyor belt 924. Access door 942 allows access for unloading of stents that have passed through oven 904. When the access doors are closed, the enclosure provides for operator safety from moving conveyor belt 924. As shown, doors 940 and 942 can include plates made from transparent material such as plastic or glass to allow viewing of the interior of loading enclosure 908. Front panel 944 and top panel 946 can also be made from a transparent material to allow viewing.

Conveyor belt 924 is directed or driven through the interior of loading enclosure 908 by gears 948, 950, and 952. One or more of the gears are drive gears which are coupled to a motor that rotates the gears and drives conveyor belt 924. In some embodiments, stents can be loaded onto barcode-labeled tracking mandrels before placement into loading enclosure 908 which can include barcode readers 956. Barcode readers 956 are in communication with a control system that keeps track of stents. Photosensors 958 are included in loading enclosure 908 near the exit of oven 904 to confirm the presence of tracking mandrels. Loading enclosure 908 can be supplied with filtered air at a positive pressure, to reduce or prevent particulate contamination from entering as access doors are opened.

FIG. 12 shows a top sectional view of device 900. Stents mounted on tracking mandrels are loaded into recesses 960 in conveyor belt 924. Conveyor belt 924 moves the mounted stents into oven 904 as shown by an arrow 964 though opening 920 and into a access tunnel 966. Conveyor belt 924 then moves the stents into the oven enclosure through the zig-zag pattern. Stents exit oven 904 through an access tunnel 968 and opening 922 into loading enclosure 908, as shown by an arrow 970.

Access tunnels 966 and 968 include revolving doors 972 and 974, respectively, to reduce temperature fluctuations within the oven enclosure. Revolving doors 972 and 974 can be coupled to idler sprockets that rotate as the chain moves to provide synchronized motion of the doors relative to the tracking mandrels. Conveyor belt 924 can move in pre-selected increments (e.g., one, two, or three inches), and dwell for a pre-selected time after each movement. The movements of conveyor belt 924 can be servo-controlled with programmable acceleration/deceleration and velocity. The movements can be between 0.5 and 1.5 seconds in duration, so that revolving doors 972 and 974 are open for very brief times to minimize exposure of the oven interior. In an incrementally moving conveyor belt 924, FIG. 12 depicts a first unloading position 990, a second unloading position 992, and a third unloading position 994.

As shown in FIG. 11, door interlocking mechanisms 941 on doors 940 and 942 prevent undesired opening of the doors while conveyor belt 924 is moving. In one embodiment, interlocking mechanisms 941 are synchronized to chain movement so that conveyor belt 924 does not move while doors 940 or 942 are open.

Figure 13:
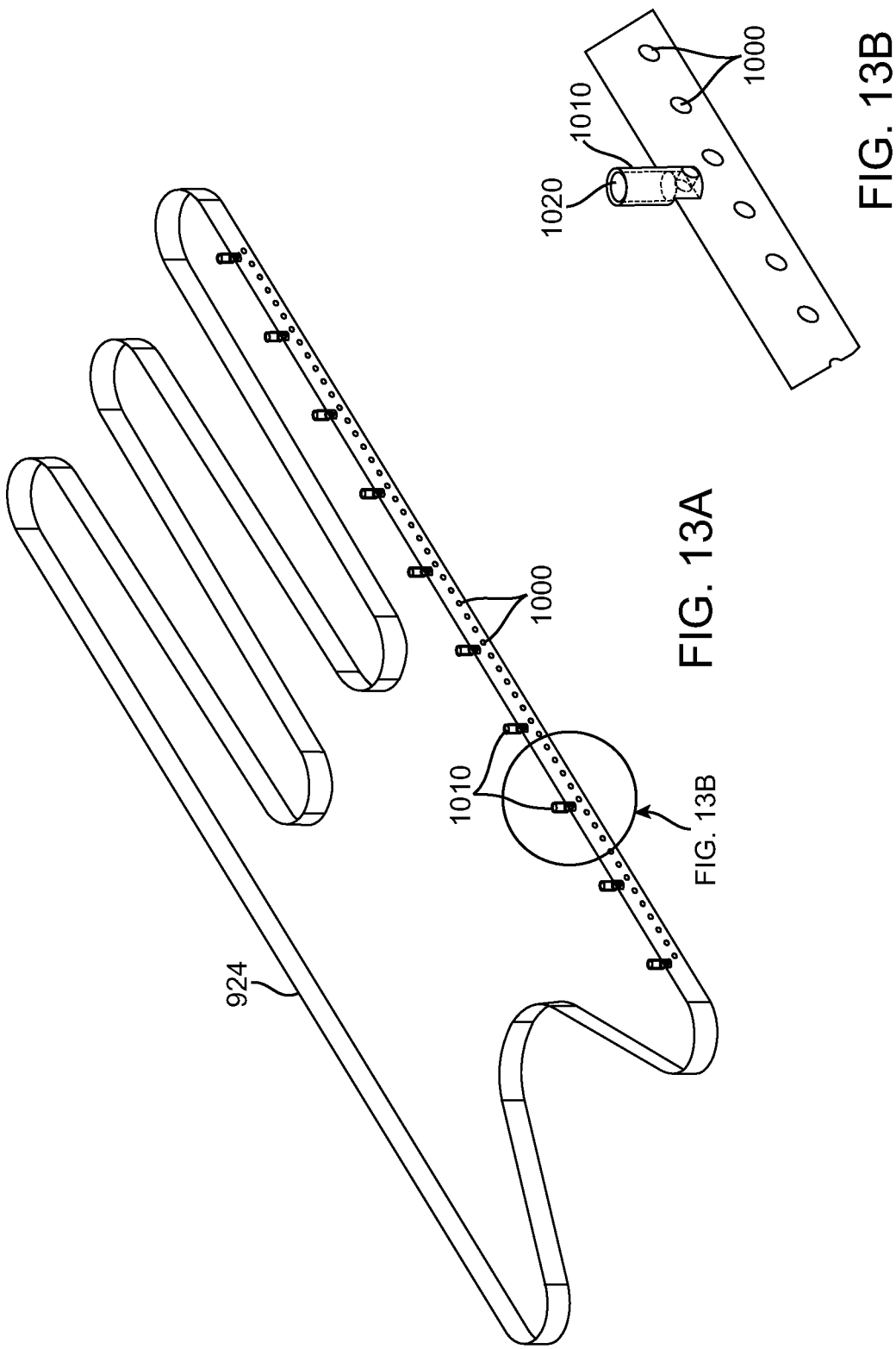
FIG. 13A depicts a close-up view of a conveyor belt.
FIG. 13B depicts stent mandrel supports in the conveyer belt of FIG. 13A.

FIG. 13A depicts a close-up view of conveyor belt 924 which includes a plurality of holes 1000 for engaging gears. Conveyor belt 924 includes a plurality of mandrel supports 1010 for supporting mandrels supporting stents. As shown in FIG. 13B, mandrel supports 1010 have a cylindrical recess 1020 in which a proximal end of a mandrel can engage.

Referring to FIG. 9, loading enclosure 908 can also include a light tower 909 that displays the status of the stents on conveyor belt 924. Light tower 909 can be in communication with sensor 958. For example, a green light can blink when a stent enters first unloading position 990. A yellow light can blink when the stent reaches second unloading position 992, and a red light can blink when the stent reaches third unloading position 994. All lights can blink if the stent is not unloaded from third unloading position 994. Sensor 958 can be in communication with a control system which can lock device 900 if a stent moves beyond third unloading station 994.

In some embodiments, sensors can be provided that detect whether and how long doors 940 and 942 are open. The sensors can be in communication with a control system that can signal an alarm system. An alarm can sound if doors 940 or 942 are left open more than a selected amount of time, e.g., 10 seconds. In addition, device 900 can lock up if doors 940 or 942 are open at indexing time or are open more than one dwell or index cycle. Additionally, the rear door can also be monitored. A dry cycle time can be adjusted for a door open time interruption. A control system can be adapted to modify the cycle time to account for interruptions due to open doors.

Figure 14:
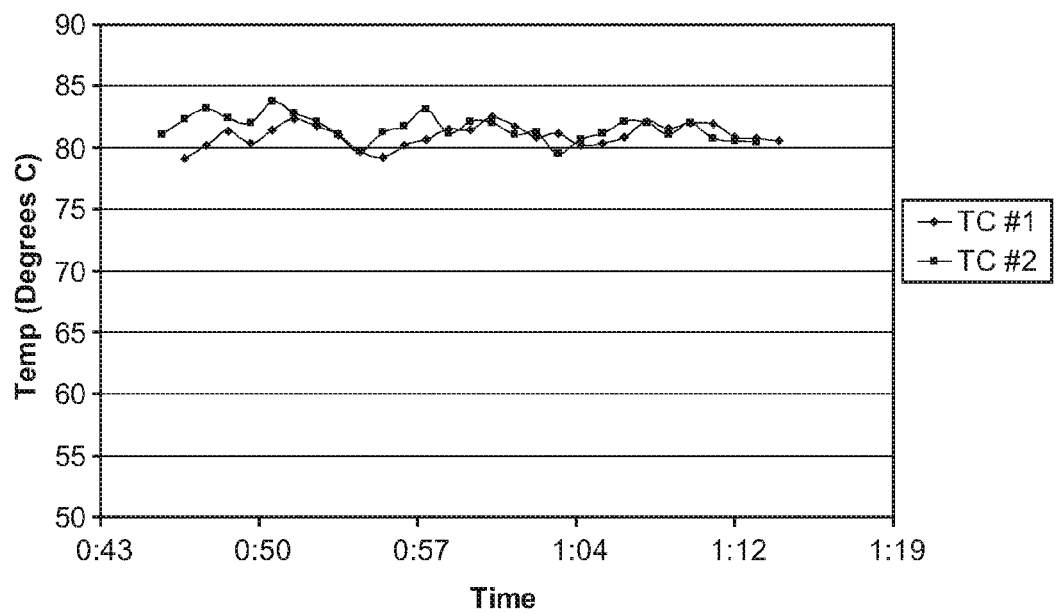
FIG. 14 depicts a plot of the temperature as a function of time within a conveyor oven.
Figure 15:
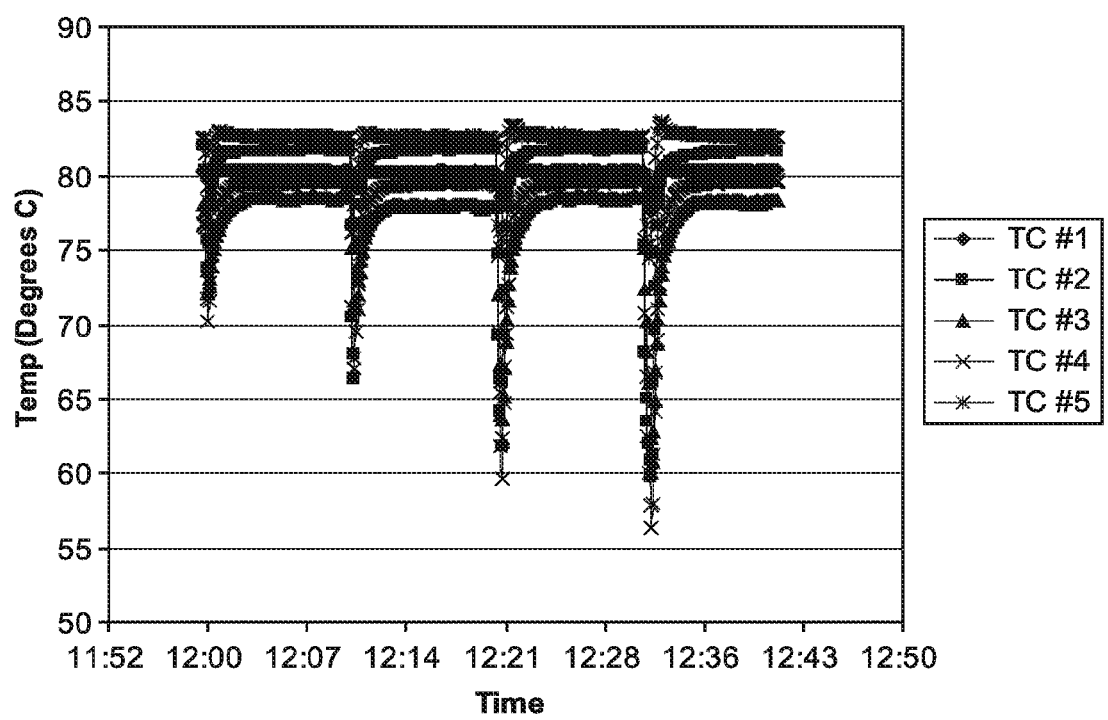
FIG. 15 depicts a plot of the temperature as a function of time within a conventional batch oven.

FIG. 14 and FIG. 15 are plots of the temperature as a function of time within a conveyor oven and a conventional batch oven, respectively. FIG. 14 includes data for two different sensors positioned within the conveyor oven. FIG.

15 includes data for five different sensors positioned within the conventional oven. In FIG. 15, the dips in the temperature correspond to openings of the door. FIG. 14 shows that the temperature in conveyor oven is relatively consistent over the time frame measured.

The baking duration of the stents can be a function of the dwell time and the length of a chain within the oven. In one exemplary embodiment, conveyor belt 924 is 105 inches with 36 stents in the oven. A dwell time of 100 seconds between chain movements provides a total baking time of 60 minutes for each stent.

Stent and Coating Materials

A non-polymer substrate for a stent may be made of a metallic material or an alloy such as, but not limited to, cobalt chromium alloy (ELGILOY), stainless steel (316L), high nitrogen stainless steel, e.g., BIODUR 108, cobalt chrome alloy L-605, "MP35N," "MP20N," ELASTINITE (Nitinol), tantalum, nickel-titanium alloy, platinum-iridium alloy, gold, magnesium, or combinations thereof "MP35N" and "MP20N" are trade names for alloys of cobalt, nickel, chromium and molybdenum available from Standard Press Steel Co., Jenkintown, Pa. "MP35N" consists of 35% cobalt, 35% nickel, 20% chromium, and 10% molybdenum. "MP20N" consists of 50% cobalt, 20% nickel, 20% chromium, and 10% molybdenum.

In accordance with one embodiment, the composition can include a solvent and a polymer dissolved in the solvent and optionally a wetting fluid. The composition can also include active agents, radiopaque elements, or radioactive isotopes. Representative examples of polymers that may be used as a substrate of a stent or coating for a stent, or more generally, implantable medical devices include, but are not limited to, poly(N-acetylglucosamine) (Chitin), Chitosan, poly(3-hydroxyvalerate), poly(lactide-co-glycolide), poly(3-hydroxybutyrate), poly(4-hydroxybutyrate), poly(3-hydroxybutyrate-co-3-hydroxyvalerate), polyorthoester, polyanhydride, poly(glycolic acid), poly(glycolide), poly(L-lactic acid), poly(L-lactide), poly(D,L-lactic acid), poly(D,L-lactide), poly(L-lactide-co-D,L-lactide), poly(caprolactone), poly(L-lactide-co-caprolactone), poly(D,L-lactide-co-caprolactone), poly(glycolide-co-caprolactone), poly(trimethylene carbonate), polyester amide, poly(glycolic acid-co-trimethylene carbonate), co-poly(ether-esters) (e.g. PEO/PLA), polyphosphazenes, biomolecules (such as fibrin, fibrinogen, cellulose, starch, collagen and hyaluronic acid), polyurethanes, silicones, polyesters, polyolefins, polyisobutylene and ethylene-alphaolefin copolymers, acrylic polymers and copolymers, vinyl halide polymers and copolymers (such as polyvinyl chloride), polyvinyl ethers (such as polyvinyl methyl ether), polyvinylidene halides (such as polyvinylidene chloride), polyacrylonitrile, polyvinyl ketones, polyvinyl aromatics (such as polystyrene), polyvinyl esters (such as polyvinyl acetate), acrylonitrile-styrene copolymers, ABS resins, polyamides (such as Nylon 66 and polycaprolactam), polycarbonates, polyoxymethylenes, polyimides, polyethers, polyurethanes, rayon, rayon-triacetate, cellulose acetate, cellulose butyrate, cellulose acetate butyrate, cellophane, cellulose nitrate, cellulose propionate, cellulose ethers, and carboxymethyl cellulose. Additional representative examples of polymers that may be especially well suited for use in fabricating embodiments of implantable medical devices disclosed herein include ethylene vinyl alcohol copolymer (commonly known by the generic name EVOH or by the trade name EVAL), poly(butyl methacrylate), poly(vinylidene fluoride-co-hexafluoropropene) (e.g., SOLEF 21508, available from Solvay Solexis PVDF, Thorofare, N.J.; Kynar 2750, available from Arkema), polyvinylidene fluoride (otherwise known as KYNAR, available from ATOFINA Chemicals, Philadelphia, Pa.), ethylene-vinyl acetate copolymers, poly(vinyl acetate), styrene-isobutylene-styrene triblock copolymers, and polyethylene glycol.

"Solvent" is defined as a liquid substance or composition that is compatible with the polymer and is capable of dissolving the polymer at the concentration desired in the composition. Examples of solvents include, but are not limited to, dimethylsulfoxide (DMSO), chloroform, acetone, water (buffered saline), xylene, methanol, ethanol, 1-propanol, tetrahydrofuran, 1-butanone, dimethylformamide, dimethylacetamide, cyclohexanone, ethyl acetate, methylethylketone, propylene glycol monomethylether, isopropanol, isopropanol admixed with water, N-methyl pyrrolidinone, toluene, and combinations thereof.

A "wetting" of a fluid is measured by the fluid's capillary permeation. Capillary permeation is the movement of a fluid on a solid substrate driven by interfacial energetics. Capillary permeation is quantified by a contact angle, defined as an angle at the tangent of a droplet in a fluid phase that has taken an equilibrium shape on a solid surface. A low contact angle means a higher wetting liquid. A suitably high capillary permeation corresponds to a contact angle less than about 90°. Representative of the wetting fluid include, but are not limited to, tetrahydrofuran (THF), dimethylformamide (DMF), 1-butanol, n-butyl acetate, dimethylacetamide (DMAC), and mixtures and combinations thereof.

Examples of radiopaque elements include, but are not limited to, gold, tantalum, and platinum. An example of a radioactive isotope is $p^{32}$. Sufficient amounts of such substances may be dispersed in the composition such that the substances are not present in the composition as agglomerates or flocs.

Active Agents

Examples of active agents include antiproliferative substances such as actinomycin D, or derivatives and analogs thereof (manufactured by Sigma-Aldrich 1001 West Saint Paul Avenue, Milwaukee, Wis. 53233; or COSMEGEN available from Merck). Synonyms of actinomycin D include dactinomycin, actinomycin IV, actinomycin $I_1$, actinomycin $X_1$, and actinomycin $C_1$. The bioactive agent can also fall under the genus of antineoplastic, anti-inflammatory, antiplatelet, anticoagulant, antifibrin, antithrombin, antimitotic, antibiotic, antiallergic and antioxidant substances. Examples of such antineoplastics and/or antimitotics include paclitaxel, (e.g., TAXOL® by Bristol-Myers Squibb Co., Stamford, Conn.), docetaxel (e.g., Taxotere®, from Aventis S.A., Frankfurt, Germany), methotrexate, azathioprine, vincristine, vinblastine, fluorouracil, doxorubicin hydrochloride (e.g., Adriamycin® from Pharmacia & Upjohn, Peapack N.J.), and mitomycin (e.g., Mutamycin® from Bristol-Myers Squibb Co., Stamford, Conn.). Examples of such antiplatelets, anticoagulants, antifibrin, and antithrombins include aspirin, sodium heparin, low molecular weight heparins, heparinoids, hirudin, argatroban, forskolin, vapiprost, prostacyclin and prostacyclin analogues, dextran, D-phe-pro-arg-chloromethylketone (synthetic antithrombin), dipyridamole, glycoprotein IIb/IIIa platelet membrane receptor antagonist antibody, recombinant hirudin, and thrombin inhibitors such as Angiomax a (Biogen, Inc., Cambridge, Mass.). Examples of such cytostatic or antiproliferative agents include angiopeptin, angiotensin converting enzyme inhibitors such as captopril (e.g., Capoten® and Capozide® from Bristol-Myers Squibb Co., Stamford, Conn.), cilazapril or lisinopril (e.g., Prinivil® and Prinzide® from Merck & Co., Inc., Whitehouse Station, N.J.), calcium channel blockers (such as nifedipine), colchicine, proteins, peptides, fibroblast growth factor (FGF) antagonists, fish oil (omega 3-fatty acid), histamine antagonists, lovastatin (an inhibitor of HMG-CoA reductase, a cholesterol lowering drug, brand name Mevacor from Merck & Co., Inc., Whitehouse Station, N.J.), monoclonal antibodies (such as those specific for Platelet-Derived Growth Factor (PDGF) receptors), nitroprusside, phosphodiesterase inhibitors, prostaglandin inhibitors, suramin, serotonin blockers, steroids, thioprotease inhibitors, triazolopyrimidine (a PDGF antagonist), and nitric oxide. An example of an antiallergic agent is permirolast potassium. Other therapeutic substances or agents which may be appropriate agents include cisplatin, insulin sensitizers, receptor tyrosine kinase inhibitors, carboplatin, alpha-interferon, genetically engineered epithelial cells, steroidal anti-inflammatory agents, non-steroidal anti-inflammatory agents, antivirals, anticancer drugs, anticoagulant agents, free radical scavengers, estradiol, antibiotics, nitric oxide donors, super oxide dismutases, super oxide dismutases mimics, 4-amino-2,2,6,6-tetramethylpiperidine-1-oxyl (4-amino-TEMPO), tacrolimus, dexamethasone, ABT-578, clobetasol, cytostatic agents, prodrugs thereof, co-drugs thereof, and a combination thereof. Other therapeutic substances or agents may include rapamycin and structural derivatives or functional analogs thereof, such as 40-O-(2-hydroxy)ethyl-rapamycin (known by the trade name of EVEROLIMUS), 40-O-(3-hydroxy)propyl-rapamycin, 40-O-[2-(2-hydroxy)ethoxy]ethyl-rapamycin, methyl rapamycin, and 40-O-tetrazole-rapamycin.

While particular embodiments of the present invention have been shown and described, it will be obvious to those skilled in the art that changes and modifications can be made without departing from this invention in its broader aspects. Therefore, the appended claims are to encompass within their scope all such changes and modifications as fall within the true spirit and scope of this invention.

What is claimed is:

1. A device for drying coated stents, the device comprising:
    an oven enclosure including a rotatable dial configured to carry stent supports within the oven enclosure so that stents on the stent supports can be conveyed by rotation of the dial within the oven enclosure to dry a coating on the stents; and
    a transfer mechanism including an actuator and a first gripper, the actuator configured to move the first gripper into and out of the oven enclosure, the first gripper configured to remove a stent support from the dial.

2. The device of claim 1, wherein the dial comprises a lip around a periphery of the dial, the lip including a plurality of holes configured to receive the stent supports.

3. The device of claim 1, wherein the oven enclosure comprises an opening sized to allow movement of the first gripper into and out of the opening.

4. The device of claim 1, further comprising a movable door that is movable to cover the opening in the oven enclosure.

5. The device of claim 4, wherein the door is movable from a bottom of the opening to a top of the opening.

6. A device for drying coated stents, the device comprising:
    an oven enclosure; and
    a conveyor belt disposed within the oven enclosure, wherein the conveyor belt is configured to support a plurality of coated stents so that the stents can be conveyed within the oven enclosure to dry a coating on the stents, the stents conveyed through movement of the belt through the oven enclosure.

7. The device of claim 6, wherein the conveyor belt comprises a plurality of holes sized to receive stent supports for carrying stents.

8. The device of claim 6, further comprising a first gear for driving the conveyor belt, the first gear disposed in the oven enclosure and engaging perforations in the conveyor belt.

9. The device of claim 6, further comprising a second gear for driving the conveyor belt, the second gear disposed outside the oven enclosure and engaging perforations in the conveyor belt.

10. The device of claim 6, wherein the conveyor belt follows a zig-zag pattern within the oven enclosure.

11. The device of claim 1, wherein the transfer mechanism further includes a second gripper, the actuator is configured to move the first gripper and the second gripper together into and out of the oven enclosure, and the second gripper is configured to place a stent support on the dial while the first gripper removes a stent support from the dial.

12. The device of claim 1, further comprising a heat source configured to heat the oven enclosure.

13. The device of claim 1, further comprising the stent supports.

14. The device of claim 6, further comprising a heat source configured to heat the oven enclosure.

15. The device of claim 14, wherein the conveyor belt includes a segment outside of the oven enclosure, the segment passes through a first opening of the oven enclosure to transport stents out of the oven enclosure and through a second opening of the oven enclosure to transport stents into the oven enclosure.

16. The device of claim 15, further comprising a first revolving door at the first opening and a second revolving door at the second opening.

17. The device of claim 15, further comprising a loading enclosure outside of the oven enclosure, the loading enclosure containing the segment of the conveyor belt that passes through the first opening and the second opening of the oven enclosure.

18. The device of claim 7, further comprising the stent supports.

* * * * *